United States Patent [19]

Luk et al.

[11] 4,374,147

[45] Feb. 15, 1983

[54] 13-OXO-MONIC ACID ESTERS USEFUL AS ANTIBACTERIAL AND ANTIMYCOPLASMAL AGENTS

[75] Inventors: Kong Luk, Horley; Norman H. Rogers, Horsham, both of England

[73] Assignee: Beecham Group Limited, England

[21] Appl. No.: 271,006

[22] Filed: Jun. 5, 1981

[30] Foreign Application Priority Data

Jun. 14, 1980 [GB] United Kingdom ............... 8019509

[51] Int. Cl.³ .................... A61K 31/35; C07D 309/06
[52] U.S. Cl. .................................. 424/283; 549/414; 542/426; 542/427
[58] Field of Search .................. 260/345.8 R, 345.7R; 542/426, 427; 424/283; 549/414

[56] References Cited

U.S. PATENT DOCUMENTS 4,205,002  5/1980  Rogers et al. ............. 260/345.8 R
4,206,224  7/1980  Clayton .............................. 424/283
4,216,223  8/1980  Clayton et al. ............ 260/345.8 R

FOREIGN PATENT DOCUMENTS 1395907  6/1971  United Kingdom ......... 260/345.8 R

Primary Examiner—Nicky Chan
Attorney, Agent, or Firm—Jacobs & Jacobs

[57] ABSTRACT

Compounds of formula (II):

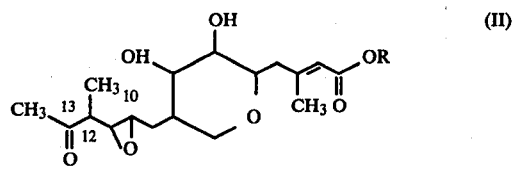

in which R represents a pharmaceutically acceptable ester-forming radical have antibacterial and antimycoplasmal activity. These compounds are produced by photo-oxidation of the corresponding 13-hydroxy compounds, optionally after having protected the glycol moiety.

7 Claims, No Drawings

13-OXO-MONIC ACID ESTERS USEFUL AS ANTIBACTERIAL AND ANTIMYCOPLASMAL AGENTS

This invention relates to antibacterial compounds and in particular to a class of pseudomonic acid and monic acid oxo-derivatives which have antibacterial activity against certain Gram-positive and Gram-negative organisms, and also possess anti-mycoplasmal activity. The derivatives are therefore of value in the treatment of human and veterinary infections.

Pseudomonic acid has the structure:

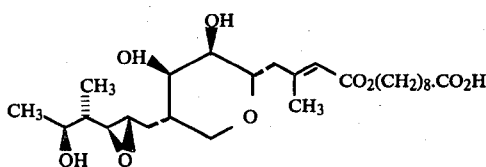

and is disclosed as having antibacterial activity in British Pat. No. 1,395,907.

German Offenlegungsschrift No. 2726619.9 discloses an acid of formula (I):

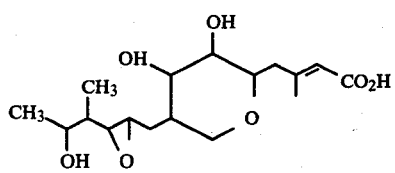

which is referred to as 'monic acid A.'

Although this compound does not appear to have antibacterial or anti-mycoplasmal activity, esters thereof do possess antibacterial and anti-mycoplasmal activity, as disclosed in the said German Offenlegungsschrift No. 2726618.8

It has now been found that certain new 13-oxo derivatives of pseudomonic acid and monic acid also possess antibacterial activity and anti-mycoplasmal activity.

According to the present invention, there is provided a compound of formula (II):

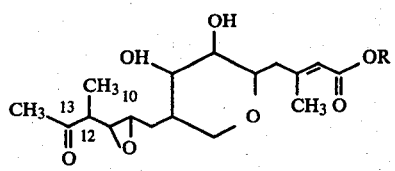

in which R represents hydrogen, a pharmaceutically acceptable ester-forming radical, or a salt-forming ion.

Suitable salts of the compound of formula (II) include metal salts e.g. aluminium, alkali metal salts, such as sodium or potassium, alkaline earth metal salts, such as calcium or magnesium, and ammonium or substituted ammonium salts for example those with lower alkylamines such as triethylamine, hydroxy-lower alkylamines such as 2-hydroxyethylamine, bis(2-hydroxyethyl)-amine, or tri(2-hydroxyethyl)-amine, cycloalkylamines such as bicyclohexylamine, or with procaine, dibenzylamine, N,N-dibenzyl-ethylene-diamine, 1-ephenamine, N-ethylpiperidine, N-benzyl-β-phenethylamine, dehydroabietylamine, N,N'-bis-dehydroabietylethylenediamine, or bases of the pyridine type such as pyridine, collidine, or quinoline.

Suitable ester-forming radicals for the group R include:

(a) $C_{1-20}$ alkyl, $C_{2-8}$ alkenyl or $C_{2-8}$ alkynyl each of which may be optionally substituted by $C_{3-7}$ cycloalkyl, halogen, carboxy, $C_{1-6}$ alkoxycarbonyl, carbamoyl, aryl, heterocyclyl, hydroxy, $C_{1-6}$ alkanoyloxy, amino, mono- and di-$(C_{1-6})$alkylamino;

(b) $C_{3-7}$ cycloalkyl optionally substituted with $C_{1-6}$ alkyl;

(c) aryl;

(d) heterocyclyl.

Each of the above groups (a), (b), (c) and (d) may be substituted by a ketonic oxo group or by a group of the formula $-SO_2-NR^XR^Y$, in which $R^X$ and $R^Y$ are the same or different and each represents (i) hydrogen or (ii) $C_{1-20}$ alkyl, $C_{2-8}$ alkenyl, either of which may be optionally substituted with $C_{3-7}$ cycloalkyl, halogen, carboxy, carbamyl, aryl, heterocyclyl, hydroxy, $C_{1-6}$ alkanoyloxy, amino, mono- or di- $(C_{1-6})$ alkylamino; or (c) $C_{3-7}$ cycloalkyl optionally substituted with $C_{1-6}$ alkyl; or (d) aryl or (e) heterocyclyl; or (f) $R^X$ and $R^Y$ together with the nitrogen atom to which they are attached represent a $C_{5-7}$ heterocyclic ring.

The term "aryl" includes phenyl and naphthyl optionally substituted with up to five halogen, $C_{1-6}$ alkyl, $C_{1-6}$ alkoxy, halo $(C_{1-6})$ alkyl, hydroxy, amino, carboxy, $C_{1-6}$ alkoxycarbonyl, or $C_{1-6}$ alkoxycarbonyl$(C_{1-6})$-alkyl groups.

The term "heterocyclyl" includes single or fused rings comprising up to four hetero atoms in the ring selected from oxygen, nitrogen and sulphur and optionally substituted with up to three halogen, $C_{1-6}$ alkyl, $C_{1-6}$ alkoxy, halo-$(C_{1-6})$-alkyl, hydroxy, amino, carboxy, $C_{1-6}$ alkoxycarbonyl, $C_{1-6}$ alkoxycarbonyl-$(C_{1-6})$-alkyl, aryl or oxo groups.

One suitable substituted ester forming radical for the group R has the formula (III):

$$-(CH_2)_nCO_2R^1 \quad\quad (III)$$

wherein n is an integer from 1 to 20 and $R^1$ is hydrogen or a pharmaceutically acceptable salt-forming ion or $C_{1-6}$ alkyl. Preferably, n is 8, i.e. the compound is a pseudomonic acid derivative.

Another sub-class of esters of formula (II) comprises those compounds wherein the group R has the formula (IIIA):

wherein n is zero or 1 to 20, $R^2$ is $C_{1-6}$ alkyl, and Q represents phenyl, $C_{1-6}$ alkyl, $C_{3-7}$ cycloalkyl, $C_{1-6}$ alkoxycarbonylmethyl, benzyl, trifluoromethylbenzyl, halobenzyl.

Preferably, within formula (IIIA) n is zero or 1 to 7, $R^2$ is methyl and Q is phenyl, methyl, iso-propyl, n-hexyl, cyclohexyl, methoxycarbonylmethyl, benzyl, 3-trifluoromethylbenzyl.

Thus the group R in compound (II) may be for example $C_{1-6}$ alkyl, in particular, methyl ethyl n-or iso-propyl, n-, sec-, iso- or tert-butyl; halo-$(C_{1-6})$-alkyl such as trifluoromethyl, 2-chloroethyl, 2,2,2-trichloroethyl; aminoalkyl groups such as aminoethyl, 2-aminoethyl, hydroxymethyl, 2-hydroxyethyl; phenyl; substituted phenyl; a benzyl group; or a group of formula (III) wherein n is an integer from 1 to 8.

A further sub-class of esters of formula (II) comprises those in which R represents $C_{1-10}$ alkyl, hydroxy-($C_{1-10}$)-alkyl, and $C_{2-8}$ alkenyl. Examples of such R groups include methyl, ethyl, isobutyl, 6-hydroxyhexyl, and allyl (i.e. prop-2-enyl).

Other specific examples of the group R include: $C_{7-20}$ alkyl groups such as heptyl, octyl, nonyl, decyl and dodecyl; cyclopropyl, cyclopropylmethyl, cyclopentyl, cyclohexyl, methoxycarbonylmethyl, 2-methoxycarbonylethyl, 3-methoxycarbonylpropyl, 4-methoxycarbonyl-n-butyl, 5-methoxycarbonyl-n-pentyl, 6-methoxy-carbonylhexyl, 7-methoxycarbonyl-n-heptyl, 10-methoxycarbonyldecyl, carbamoylmethyl, benzyl, 2,4,6-trichlorophenyl, pentachlorophenyl, o-, m- or p-methyl-phenyl, o-, m- or p-methoxycarbonylphenyl, 2- or 3- or 4-pyridyl, prop-2-ynyl, 2-dialkylaminoethyl or 3-methoxycarbonylprop-2-enyl.

This invention also provides a pharmaceutical or veterinary composition which comprises a compound of formula (II) together with a pharmaceutically or veterinary acceptable carrier or excipient.

The compositions may be formulated for administration by any route, and would depend on the disease being treated. The compositions may be in the form of tablets, capsules, powders granules, lozenges, liquid or gel preparations, such as oral, topical or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl-pyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin, hydrogenated edible fats; emulsifying agents, for example lecithin, sorbitan monooleate, or acacia; non aqueous vehicles (which may include edible oils), for example almond oil, fractionated coconut oil, oily esters such glycerine, propylene glycol, or ethyl alcohol; preservatives, for example methyl or propyl p-hydroxybenzoate or sorbic acid, and if desired conventional flavouring or colouring agents.

For topical application to the skin compounds of this invention may be made up into a cream, lotion or ointment. Cream or ointment formulations that may be used for compounds of formula (II) are conventional formulations well known in the art, for example, as described in standard text books of pharmaceutics and cosmetics such as Harry's Cosmeticology published by Leonard Hill Books, and the British Pharmacopoeia.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can either be suspended or dissolved in the vehicle. In preparing solutions the compound can be dissolved in water for injection and filter sterilized before filling into a suitable vial or ampoule and sealing. Advantageously, adjuvants such as a local anaesthetic, preservative and buffering agents can be dissolved in the vehicle. To enhance the stability the composition can be frozen after filling into the vial and water removal under vacuum. The dry lyophilized powder is then sealed in the vial. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compounds.

Veterinary compositions for intrammary treatment of mammary disorders in animals, especially bovine mastitis, will generally contain a suspension of a compound of formula (II) in an oily vehicle.

The compositions may contain from 0.1% to 99% by weight, preferably from 10–60% by weight, of the active material, depending on the method of administration. Where the compositions comprise dosage units, each unit will preferably contain from 50–500 mg, of the active ingredient. The dosage as employed for adult human treatment will preferably range from 100 mg to 3 g, per day, for instance 250 mg to 2 g, per day, depending on the route and frequency of administration.

Alternatively a compound of formula (II) may be administered as part of the total dietary intake. In this case the amount of compound employed may be less than 1% by weight of the diet and in preferably no more than 0.5% by weight. The diet for animals may consist of normal foodstuffs to which the compound may be added or it may be added to a premix.

A suitable method of administration of a compound of formula (II) to animals is to add it to the animals drinking water. In this case a concentration of compound in the drinking water of about 5–500 µg/ml, for example 5–200 µg/ml, is suitable.

The compound of formula (II) may be prepared by photooxidation of the corresponding 13-hydroxy compound. Preferably, the process is carried out by irradiating the corresponding 13-hydroxy compound with ultra violet light in the presence of benzophenone, and separating the 13-oxo compound from the reaction mixture by chromatography. The reaction is suitably carried out in the presence of a non-polar solvent, preferably benzene.

In a more preferred process, the compound of formula (II) can be prepared by treating the corresponding 13-hydroxy compound with a glycol protecting agent, followed by oxidation with a non acidic oxidising agent.

Suitable glycol protecting reagents include compounds of formula (IV):

wherein $R^3$ is hydrogen or a $C_{1-6}$ alkyl group and $R^4$, $R^5$ and $R^6$ independently represent a $C_{1-6}$ alkyl group.

The group R³ may be for example hydrogen, methyl, ethyl, n- or iso-propyl. Most suitably, R³ represents hydrogen so that the compound of formula (IV) is a trialkyl orthoformate.

Groups R⁴, R⁵ and R⁶ may be for example, methyl, ethyl, n- or iso-propyl, n-, iso-, sec- or tert-butyl. Preferably R⁴, R⁵ and R⁶ are all the same and each represents a methyl group. The preferred compound of formula (IV) is trimethylorthoformate.

A further, particularly useful glycol protecting reagent is 1-(N,N-dimethylamino)ethylidene acetal which converts the glycol moiety to the structure.

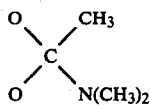

Conveniently the glycol protected derivative of the 13-hydroxy compound, which is prepared by treating the compound with the glycol-protecting reagent, is oxidised to give a glycol protected oxo-derivative. This derivative is then deprotected to give the desired 13-oxo compound.

A typical reaction scheme for this process, using trimethyl orthoformate, is shown below:

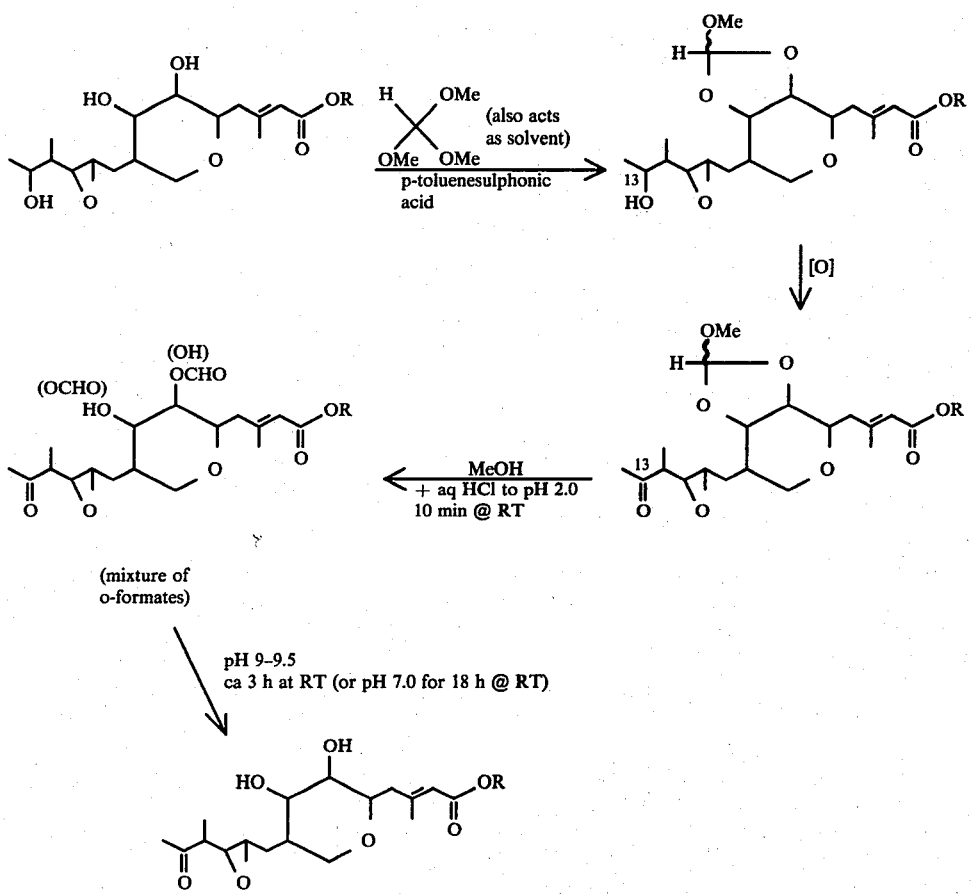

If 1-(N,N-dimethylamino)ethylidene acetal is employed, the glycol protection reaction is suitably carried out in an organic solvent, preferably chloroform, at ambient temperature. The protected derivative is then oxidised, and deprotection carried out by refluxing in an aqueous lower alkanolic solution, preferably methanol, to give the desired 13-oxo compound.

Preferred non-acidic oxidising agents include chromium trioxide/pyridine (Sarett's reagent), pyridinium dichromate, or pyridinium chlorochromate.

The following examples illustrate the preparation of a number of compounds of the invention:

EXAMPLE 1

Methyl 13-Oxopseudomonate A

Methyl pseudomonate (100 mgs) was dissolved in trimethylorthoformate (3 mls), 2 crystals pTSA added, and stirred for 5 minutes. The solution was diluted with ether, washed with dilute NaHCO₃ solution and brine, dried (MgSO₄) and evaporated in vacuo. The resulting oil was dissolved in pyridine (1 ml), treated with Sarett's reagent and stirred overnight at room temperature. (Sarett's reagent:—to pyridine (1 ml) at 15°–20° C. was added chromium trioxide (100 mg) portionwise and with stirring. The chromium trioxide dissolved at first, but then the yellow complex precipitated. The reaction was kept below 30° C. (Feiser and Feiser p. 145). The slurry was added directly to the ester in pyridine).

The reaction mixture was poured into water (10 mls), extracted into ether (10 mls) and the ether phase washed with water, brine, dried (MgSO₄) and evaporated in vacuo. The resulting oil was deprotected by dissolving in methanol/water; 10 mls/3 mls, adjusting the pH to 2.0 and stirring for 15 minutes. The pH was then adjusted to 9.0–9.5 where it was maintained until the pH was stable (ca 3 hours). The pH was adjusted to 7.0, the solution evaporated in vacuo, and the residue dissolved in ethyl acetate, washed with dilute NaHCO$_3$ solution and brine, dried (MgSO$_4$) and evaporated *in vacuo* to yield an oil which gave 3 spots on tlc (chloroform/methanol: 9/1). Separation on a silica column (type 60, 1.5 g) eluting with a gradient of 0.5%–1.0% methanol-chloroform gave the product as an oil (0.023 g, 23.0%). [α]$^{20}$ −29.3° (c, 0.3% CHCl$_3$), $\nu_{max}$ (CHCl$_3$), 2930, 2860, 1720 and 1645 cm$^{-1}$; λ$^D$ max EtOH) 221 nm (εm 14,200); δ$_H$ (CDCl$_3$) 5.77 (1H, s, vinylic H), 4.05 (2H, t, CH$_2$—9′), 3.64 (3H, s, OCH$_3$), 2.36 (3H, d, CH$_3$—14), 2.20 (3H, s, vinylic CH$_3$), 1.32 (methylene envelope), 1.14 (3H, d, CH$_3$—17); δ$_C$ (CDCl$_3$) 209.8 (C13), 174.2 (C1′), 166.8 (C1), 156.6 (C3), 117.7 (C2), 74.9 (C5), 70.4 (C7), 69.0 (C6), 65.3 (C16), 63.8 (C9′), 59.0 (C11), 56.3 (C10), 51.4 (OMe), 49.2 (C12), 42.9 (C4), 39.6 (C8), 34.1 (C2′), 31.5 (C9), 29.6 (C14), 29.1 (C4′, C5′, C6′), 28.7 (C8′), 26.0 (C7′), 24.9 (C3′), 19.1 (C15), 12.3 (C17); (Found: C, 63.36; H, 8.78%. C$_{27}$H$_{44}$O$_9$ requires C, 63.25; H, 8.67%).

EXAMPLE 2

Methyl 13—Oxopseudomonate A

A solution of methyl pseudomonate A (0.384 g) and benzophenone (0.545 g) in benzene (100 ml) was irradiated with a Hanovia 450 W. medium pressure lamp at room temperature and h.p.l.c. analysis on a silica column was made every 2 hours to monitor the reaction. The reaction was stopped after 12 hours and the solvent evaporated to give a very complex mixture. This was then eluted through a column of silica gel (20 g). Elution of the column with 4% methanol in chloroform afforded 3 fractions. The first fraction was an oil (0.05 g) which was ca 95% one compound (H.p.l.c.) and upon purification by preparative t.l.c. (developed 3 times with 8% methanol in chloroform, Rf=0.6) gave the desired methyl 13-oxopseudomonate A (0.05 g).

The second fraction from the column was also an oil (0.02 g) and was ca 70% pure (H.p.l.c.). Further purification by preparative t.l.c. (developed 3 times with 8% methanol in chloroform, Rf=0.5) afforded methyl isopseudomonate A (Z-isomer); λ max 219 (εm 11600) nm; $\nu_{max}$ (CHCl$_3$) 1730, 1690, 1650, 1195, 1155, and 1085 cm$^{-1}$; δ$_H$ (CDCl$_3$) 5.78 (1H, m, —CH=), 3.65 (3H, s, CO$_2$CH$_3$), 2.01 (3H, d, J=1.5 Hz, $_{CH_3}$C=C), 1.20 (3H, d, J=7 Hz), and 0.93 (3H, d, J=7 Hz); m/e (relative intensity) 514 (1.5), 496 (2.5) 483 (3), 478 (4), 465 (3), 452 (4), 433 (4.5), 434 (4.5), 412 (6.5), 366 (44), 270 (87), 227 (100), and 209 (32). (Found, M+ 514.3116. C$_{27}$H$_{46}$O$_9$ requires M+ 514.3141).

The third fraction eluted from the column was found to be the starting material (0.05 g).

EXAMPLE 3

13—Oxopseudomonic acid A

Methyl 13—oxopseudomonate A (0.075 g) was dissolved in DMF (8 ml) and 0.05 M phosphate buffer pH 7.0 (40 ml) was added followed by bakers' yeast (1.7 g). After stirring for 18 hours the mixture was centrifuged. The supernatant was removed. The solid residue was washed with ethanol and re-centrifuged. The supernatant and washings were evaporated to dryness. The residue was digested with ethanol, filtered and the filtrate evaporated *in vacuo* to dryness. The resulting residue was partitioned between ethyl acetate and brine and the pH adjusted to 3.0 with N/10 hydrochloric acid. The ethyl acetate layer was separated washed with brine, dried (MgSO$_4$) and evaporated *in vacuo* to give an oil. The oil was purified by column chromatography on silica gel eluting with 2% methanol/chloroform. Pure 13—oxopseudomonic acid A was obtained as an oil (0.053 g). δc (CDCl$_3$), 210.1 (C13), 178.2 (C1′), 166.9 (C1), 156.6 (C3), 117.6 (C2), 74.9 (C5), 70.4 (C7), 69.1 (C6), 65.3 (C16), 63.9 (C9′), 59.0 (C11), 56.4 (C10), 49.2 (C12), 42.8 (C4), 39.5 (C8), 33.9 (C2′), 31.5 (C9), 29.3 (C14), 28.9 (C4′, C5′, C6′), 28.9 (C8′), 25.9 (C7′), 24.7 (C3′), 19.1 (C15), 12.3 (C17).

EXAMPLE 4

Sodium 13—Oxopseudomonate A

Pseudomonic acid (2 g) was dissolved in MDC (50 ml), trimethylorthoformate (0.4 ml) and 10 mgs pTSA added, and stirred for 5 minutes. After evaporation to dryness, pyridine (20 ml) was added followed by Sarrett reagent (2 g CrO$_3$ in 20 ml pyridine), and stirred overnight at room temperature. The mixture was poured into water (200 ml) and extracted with ether (2×20 ml). The ether fraction was washed with water, brine, dried (MgSO$_4$), then evaporated to dryness. The resulting residue was dissolved in methanol/water (100 mls/30 mls), stirred at pH 2.0 for 15 minutes, and then at pH 8.5–9.0 for 3 hours. The pH was adjusted to 3.0, the solution evaporated to dryness, and the residue dissolved in ethyl acetate. The solution was washed with water and brine, dried (MgSO$_4$) and evaporated in vacuo to give an oil. Separation on a silica column (type 60, 20 g) eluting with a gradient of 2%–5% methanol/chloroform gave the product as an oil (0.180 g, 9.04%). This oil was converted into sodium 13-oxopseudomonate A hemihydrate. [α]$_D^{20}$ −53.2°, (c, 1% EtOH); $\nu_{max}$ (KBr) 2920, 2850, 1710 and 1642 cm$^{-1}$; λ$_{max}$ (EtOH) 223 nm (εm 13,700); δ$_H$ (D$_2$O) 5.75 (1H, s, vinylic H), 4.09 (2H, t, CH$_2$—9), 2.25 (3H, s, CH$_3$—14), 2.12 (3H, s, vinylic CH$_3$), 1.28 (methylene envelope), 1.17 (3H, d, CH$_3$—17); (Found: C, 58.85; H, 7.64%. C$_{26}$H$_{41}$O$_9$ Na. ½H$_2$O requires C, 58.95; H, 8.01%).

EXAMPLE 5

Ethyl 13—oxomonate A (Ethyl 4-(5-(2,3-epoxy-4-methyl hexan-5-onyl)-3,4-dihydroxytetrahydropyran-2-yl)-3-methylbut-2-enoate).

Ethyl monate A (1 g, 2.7 mmol) was dissolved in trimethyl orthoformate (30 ml) and p-toluenesulphonic acid (10 mg) was added. The resulting solution was stirred 5 min at 20°, then diluted with ether, washed with aqueous sodium bicarbonate, then with brine, dried (MgSO$_4$) and evaporated in vacuo. The residue was dissolved in methylene chloride (20 ml), the resulting solution cooled to 0°, and pyridinium chlorochromate (0.65 g, 3 mmol) added. This mixture was stirred 16 h at 20°, ether was then added, and the mixture filtered through Celite. The filtrate was evaporated in vacuo and the residue partitioned between ethyl acetate/ether and water (pH buffered to 6.5). The organic fraction was dried, filtered, and evaporated in vacuo to leave a brown oil (1.3 g). This was dissolved in 50% aqueous ethanol and the pH adjusted to 2.0. After 10 min the pH was adjusted to 8.5 and kept at 8.5 for 1 h. It was then adjusted to 7.0 and the resulting solution evaporated to small volume in vacuo and then partitioned between ethyl acetate and aqueous sodium bicarbonate. The organic layer was washed twice with water, dried, and evaporated in vacuo to leave a colourless oil (0.54 g), which was purified by chromatography (30 g silica, 0 to 2% methanol in chloroform) to give pure ethyl 13-oxomonate A as a colourless oil (0.135 g, 13%), $\nu_{max}$ (CHCl$_3$) 3420 (broad), 1705, 1645, 1150, 730 cm$^{-1}$; $\lambda_{max}$ 221 nm ($\epsilon$m 13,500); $\delta$H (CDCl$_3$) 5.74 (1H, s, H2), 4.13 (2H, q, H1'), 2.19, 2.21 (6H, 2s, CH$_3$—14, CH$_3$—15), 1.25 (3H, t, CH$_3$—2'), 1.12 (3H, d, CH$_3$—17); $\delta$C (CDCl$_3$), 210.0 (C13), 166.8 (C1), 156.7 (C3), 117.7 (C2), 74.9 (C5), 70.5 (C7), 69.1 (C6), 65.3 (C16), 59.6 (C1'), 59.0 (C11), 56.4 (C10), 49.3 (C12), 42.9 (C4), 39.6 (C8), 31.5 (C9) 29.4 (C14), 19.1 (C15), 14.3 (C2'), 12.4 (C17); m/e (relative intensity) 370 (M$^+$, 1%), 352 (M$^+$—H$_2$O, 16), 225 (18), 109 (100) (Found: 352.1876. C$_{19}$H$_{28}$O$_6$ requires 352.1867).

Biological Data (a) Human Bacteria

Table 1 shows the MIC values ($\mu$g/ml) of the compounds of Examples 1, 4 and 5 against a number of organisms important in human infections obtained by serial dilution in nutrient agar containing 5% "chocolated" horse blood.

TABLE 1

| | Compound of Example No. | | |
|---|---|---|---|
| ORGANISM | 1 | 4 | 5 |
| E.coli NCTC 10418 | >200 | >100 | >100 |
| E.coli ESS | 2.0 | 2.5 | 10.0 |
| P. mirabilis 889 | >200 | >100 | 100 |
| K. aerogenes A | >200 | >100 | >100 |
| Ps. aeruginosa 10662 | >200 | >100 | >100 |
| Pasteurella multocida 1633 | 1.0 | — | 10.0 |
| Haemophilus influenzae Q1 | 0.5 | 0.05 | 1.0 |
| Haemophilus influenzae Wy21 | 0.5 | 0.1 | 1.0 |
| Neisseria catarrhalis 1502 | 1.0$^a$ | 0.5 | 2.5 |
| Bacillus subtilis 6633 | 0.5 | 0.1 | 10.0 |
| Corynebacterium xerosis 9755 | >200 | >100 | — |
| Sarcina lutea 8340 | >200 | >100 | — |
| Staph.aureus Oxford | 0.5 | 0.2 | 5.0 |
| Staph.aureus Russell | 2.0 | 0.5 | 5.0 |
| Staph.aureus 1517 | — | — | 5.0$^b$ |
| Strep.faecalis I | >200 | >100 | >100 |
| Strep.pyogenes A 64/848 | 0.5 | 1.0 | 50 |
| Strep.pyogenes B 2788 | 10 | 1.0 | 50 |
| Strep.pyogenes C 2761 | 2.0 | 0.5 | 100 |
| Strep.pneumoniae CN33 | — | 0.5 | 10 |

$^a$Neisseria flavesceus 8263
$^b$Staph. aureus W2827

(b) Veterinary Bacteria

Table 2 shows the MIC values ($\mu$g/ml) of the compounds of Examples 4 and 5 against a number of organisms important in veterinary infections.

The MIC values were determined by agar dilution using diagnostic sensitivity test agar (Oxoid) using a multipoint inoculator delivering 0.001 ml of an inoculum adjusted to give 10$^7$–10$^8$ organisms per ml and read after 24 hours incubation at 37° C.

TABLE 2

| | Compound of Example No. | |
|---|---|---|
| Organism | 4 | 5 |
| E.coli NCTC 10418 | >80 | >80 |
| E.coli E1 | >80 | >80 |
| S.dublin S7 | >80 | >80 |
| S.typhimurium S18 | >80 | >80 |
| Bord.bronchiseptica BO8 | 80 | >80 |
| Bord.bronchiseptica BO9 | 80 | 80 |
| Past.multocida PA1 | 0.625 | 2.5 |
| Past.multocida PA2 | 0.625 | 0.625 |
| Past.haemolytica PA5 | 10 | 10 |
| Erysipelothrix rhusiopathiae NCTC 8163 | >80 | >80 |
| Corynebacterium pyogenes CY1 | >80 | >80 |

TABLE 2-continued

| | Compound of Example No. | |
|---|---|---|
| Organism | 4 | 5 |
| Staph.aureus B4 (pen resis) | 1.25 | .625 |
| Staph.aureus 152 (pen sens) | 1.25 | 0.625 |
| Staph.aureus Oxford | 1.25 | 0.625 |
| Strep.suis (group D) SPS11 | 20 | >80 |
| Strep.uberis SPU1 | 0.312 | 2.5 |
| Strep.dysgalactiae SPD1 | 1.25 | 20 |
| Strep.agalactiae SPA1 | 10 | 20 |
| B. subtilis ATCC 6633 | >80 | NG |

(c) Anti-Mycoplasmal Activity

Table 3 shows the in vitro MIC values ($\mu$g/ml) of the compounds of Examples 1, 4 and 5 against a number of mycoplasma organisms.

| | Compound of Example No. | | |
|---|---|---|---|
| ORGANISM | 1 Broth* | 4 Broth* | 5 Agarose+ |
| M.suipneumoniae Str.11 | — | — | 2.5 |
| M.suipneumoniae J2206/183b | 62.5 | 31.25 | 5.0 |
| M.hyorhinis ATCC 23234 | — | — | 5.0 |
| M.hyosynoviae ATCC 25591 | — | — | 2.5 |
| M.bovis NCTC 10131 | — | — | 0.1 |
| M.dispar NCTC 10125 | 0.5 | 3.9 | 1.0 |
| M.pneumoniae (Mac) ATCC 15492 | — | — | >10 |
| M.pneumoniae 427a | 250 | 250 | — |

*Determined by serial dilution in Friis broth (Friis N.F. 1975. Nord. Vet. Med. 27, 337) in microtiter plates using a modification of the metabolite inhibition test (Taylor-Robinson D. 1967. Postgrad. Med. J., 43, suppl. March, page 100.
+Determined in Friis broth solidified with 0.9% agarose. The inoculum was 10$^3$ to 10$^5$ C.F.U. MIC's were recorded after 6 days incubation at 37° C.

We claim:

1. A compound of formula (II):

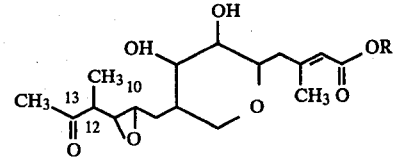

in which R is a pharmaceutically acceptable ester-forming radical.

2. A compound of formula (II) according to claim 1 wherein R is an ester-forming radical selected from optionally substituted C$_{1-20}$ alkyl, C$_{2-8}$ alkenyl, C$_{2-8}$ alkynyl, C$_{3-7}$ cyclo-alkyl, aryl and heterocyclyl.

3. The compound according to claim 1, wherein R is —(CH$_2$)$_n$CO$_2$R$^1$, wherein n is an integer of from 1 to 20 and R$^1$ is hydrogen, alkyl of 1 to 6 carbon atoms or a pharmaceutically acceptable salt-forming ion.

4. The compound according to claim 3, wherein n is 8.

5. An anti-bacterial or anti-mycoplasmal pharmaceutical composition comprising an effective amount of the pharmaceutically acceptable ester according to claim 1 or a pharmaceutically acceptable salt of said ester where said ester-forming radical is substituted by carboxy in combination with a pharmaceutically acceptable carrier therefor.

6. A composition according to claim 5 wherein the carrier is drinking water or feedstuff provided for animals.

7. A method for treating bacterial or mycoplasmal infections of humans or animals, comprising the administration of an effective, non-toxic amount of the pharmaceutically acceptable ester according to claim 1 or a pharmaceutically acceptable salt of said ester where said ester-forming radical is substituted by carboxy, to the infected human or animal.

* * * * *